(12) United States Patent  (10) Patent No.: US 8,633,316 B2
Sugita et al.  (45) Date of Patent: Jan. 21, 2014

(54) PRODUCING METHOD OF NITROGEN CONTAINING CONDENSED HETEROCYCLIC COMPOUND

(75) Inventors: Shuichi Sugita, Tokyo (JP); Eisaku Katoh, Tokyo (JP); Rie Fujisawa, Kanagawa (JP)

(73) Assignee: Konica Minolta Holdings, Inc., Tokyo (JP)

( * ) Notice: Subject to any disclaimer, the term of this patent is extended or adjusted under 35 U.S.C. 154(b) by 310 days.

(21) Appl. No.: 13/009,989

(22) Filed: Jan. 20, 2011

(65) Prior Publication Data

US 2011/0184176 A1  Jul. 28, 2011

(30) Foreign Application Priority Data

Jan. 25, 2010  (JP) .................. 2010-012926

(51) Int. Cl.
*C07D 209/82* (2006.01)
*C07D 209/58* (2006.01)

(52) U.S. Cl.
USPC ............... 546/79; 548/427; 548/452

(58) Field of Classification Search
USPC ................ 546/79; 548/427, 452
See application file for complete search history.

(56) References Cited

U.S. PATENT DOCUMENTS

| | | | |
|---|---|---|---|
| 5,576,460 | A | 11/1996 | Buchwald et al. |
| 6,759,554 | B2 | 7/2004 | Buchwald et al. |
| 6,867,298 | B2 | 3/2005 | Buchwald et al. |

FOREIGN PATENT DOCUMENTS

JP  10-199742  7/1998

*Primary Examiner* — Rita Desai

(74) *Attorney, Agent, or Firm* — Lucas & Mercanti, LLP

(57) ABSTRACT

Provided is a method for producing a nitrogen-containing condensed heterocyclic compound containing the step of: reacting a compound represented by Formula (1a) or Formula (1b) with a compound represented by Formula (2) under existence of cupper or a cupper ion, and a ligand to produce a nitrogen-containing condensed heterocyclic compound represented by Formula (3a) or Formula (3b):

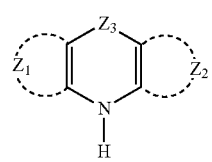

Formula (1a)

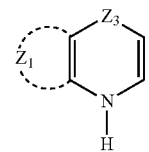

Formula (1b)

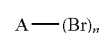

Formula (2)

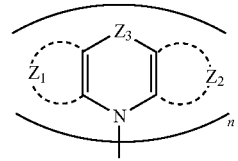

Formula (3a)

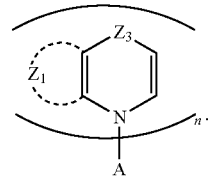

Formula (3b)

5 Claims, No Drawings

PRODUCING METHOD OF NITROGEN CONTAINING CONDENSED HETEROCYCLIC COMPOUND

CROSS REFERENCE TO RELATED APPLICATIONS

This application is based on Japanese Patent Application No. 2010-012926 filed on Jan. 25, 2010 with Japan Patent Office, the entire contents of which are hereby incorporated by reference.

TECHNICAL FIELD

The present invention relates to a production method of a nitrogen-containing condensed heterocyclic compound useful as an intermediate of an organic synthetic compound or an organic electroluminescence material.

BACKGROUND

As a synthetic method which forms a C—N bond from an aryl halide and an amine compound, a method of performing under existence of a Pd catalyst is known widely (refer to Patent document 1). Moreover, a method of using highly active $P(tBu)_3$ as a ligand is known (refer to Patent document 2). However, when a compound which carries out poisoning of a Pd catalyst, for example, a nitrogen-containing condensed heterocyclic compound was used, there was a problem that a reaction did not advance or an excessive amount of catalyst was required. Further, although Ullmann reaction is known as a method of forming a C—N bond, when an aromatic bromide is used, reactivity is low and application thereof is difficult. Although a method of reacting under existence of copper or a copper ion, and a ligand is disclosed as another method of forming a C—N bond, there is no disclosure using a nitrogen-containing condensed heterocyclic compound like the present invention as a reaction substrate (refer to Patent documents 3 and 4, non-patent documents 1 and 2).

Patent document 1: U.S. Pat. No. 5,576,460
Patent document 2: Japanese Patent No. 3161360
Patent document 3: U.S. Pat. No. 6,759,554
Patent document 4: U.S. Pat. No. 6,867,298
Non-patent document 1: D. A. K. Vezzu et al, Org. Lett., volume 11, page 4310 (2009)
Non-patent document 2: A. Shafir et al, J. Am. Chem. Soc., volume 128, page 8742 (2006)

SUMMARY

The present invention was made in view of the above-mentioned problems, and an object of the present invention is to provide a producing method of a nitrogen-containing condensed heterocyclic compound with a low catalyst amount and high yield, even when an aromatic bromide is used as a raw material.

The above-described object of the present invention is attained by the following embodiments.

1. A method for producing a nitrogen-containing condensed heterocyclic compound comprising the step of:
reacting a compound represented by Formula (1a) or Formula (1b) with a compound represented by Formula (2) under existence of copper or a cupper ion, and a ligand to produce a nitrogen-containing condensed heterocyclic compound represented by Formula (3a) or Formula (3b).

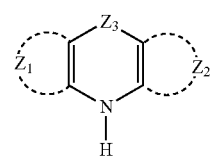

Formula (1a)

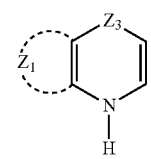

Formula (1b)

A—(Br)$_n$

Formula (2)

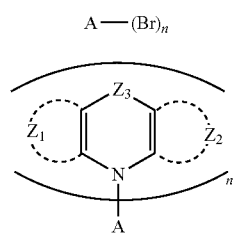

Formula (3a)

Formula (3b)

In the above-described Formulas, "A" represents an aromatic hydrocarbon ring or an aromatic heterocycle; $Z_1$ represents a non-metallic atomic group necessary to from an aromatic heterocycle; $Z_2$ represents a non-metallic atomic group necessary to from an aromatic hydrocarbon ring or an aromatic heterocycle; $Z_3$ represents a single bond or a divalent linking group; and "n" represents an integer of 1 to 4.

2. The method for producing a nitrogen-containing condensed heterocyclic compound of claim 1, wherein the compound represented by Formula (1a) is represented by Formula (4a), the compound represented by Formula (1b) is represented by Formula (4b), the compound represented by Formula (3a) is represented by Formula (5a), and the compound represented by Formula (3b) is represented by Formula (5b).

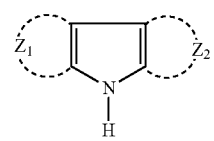

Formula (4a)

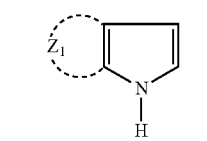

Formula (4b)

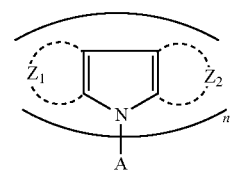

Formula (5a)

Formula (5b)

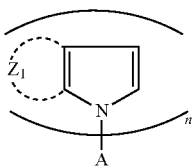

In the above-described Formulas, "A" represents an aromatic hydrocarbon ring or an aromatic heterocycle; $Z_1$ represents a non-metallic atomic group necessary to from an aromatic heterocycle; $Z_2$ represents a non-metallic atomic group necessary to from an aromatic hydrocarbon ring or an aromatic heterocycle; and "n" represents an integer of 1 to 4.

3. The method for producing a nitrogen-containing condensed heterocyclic compound as described in the above-described items 1 or 2, wherein the ligand is a pyridine compound, or β-diketone compound.

4. The method for producing a nitrogen-containing condensed heterocyclic compound as described in any one of the above-described items 1 to 3, wherein the reaction is carried out under existence of a base.

According to the present invention, it is possible to provide a producing method of a nitrogen-containing condensed heterocyclic compound with a low catalyst amount and high yield, even when an aromatic bromide is used as a raw material.

It can be produced a nitrogen-containing condensed heterocyclic compound useful as an intermediate of an organic synthetic compound or an organic electroluminescence material by using the method of the present invention with a low catalyst amount and a high yield, and the method of the present invention exhibits an excellent effects.

DESCRIPTION OF PREFERRED EMBODIMENT

Although the embodiments for carrying out the present invention will be described hereafter, the present invention will not be limited to these.

Hereafter, the present invention will be further described in details.

In the aforesaid Formulas (1a), (1b), (3a) and (3b), $Z_1$ and $Z_2$ each represents a non-metallic atomic group necessary to from an aromatic heterocycle. Examples of the aromatic heterocycle include: a furan ring, a thiophene ring, a pyridine ring, a pyridazine ring, a pyrimidine ring, a pyrazine ring, a triazine ring, a benzimidazole ring, an oxadiazole ring, a triazole ring, an imidazole ring, a pyrazole ring, a thiazole ring, an indole ring, a benzimidazole ring, a benzothiazole ring, a benzooxazole ring, a quinoxaline ring, a quinazoline ring, a phthalazine ring and an oxazole ring.

In the aforesaid Formulas (1a) and (3a), $Z_2$ also represents a non-metallic atomic group necessary to from an aromatic hydrocarbon ring. Examples of the aromatic hydrocarbon ring include: a benzene ring, a biphenyl ring, a naphthalene ring, an azulene ring, an anthracene ring, a phenanthrene ring, a pyrene ring, a chrysene ring, a naphthacene ring, a triphenylene ring, a o-terphenyl ring, a m-terphenyl ring, a p-terphenyl ring, an acenaphthene ring a coronene ring, a fluorene ring, a fluoranthrene ring, a naphthacene ring, a pentacene ring, a perylene ring, a pentaphene Ting, a picene ring, a pyranthrene ring, an anthraanthrene ring, a dibenzofuran ring, a dibenzothiophene ring and a carbazole ring. Among these, especially preferable is a benzene ring.

$Z_3$ represents a single bond or a divalent linking group. Examples of a divalent linking group represented by $Z_3$ are: a hydrocarbon group such as an alkylene group, an alkenylene group and an arylene group. It may be a divalent linking group containing a hetero atom, and it may be a divalent linking group derived from a compound containing an aromatic hetero cycle (it is called as a hetero aromatic compound) such as a thiophene-2,5-diyl group and a pyrazine-2,3-diyl group. Further, it may be a chalcogen atom such as an oxygen atom and a sulfur atom. Moreover, it may be a linked group through a hetero atom such as an alkyl-imino group and a dialkyl silane diyl group and a diaryl germane diyl group. A mere single bond represented by $Z_3$ is a single bond which binds the substituents to connect directly with each other. Among the aforesaid linking groups represented by $Z_3$, most preferable is a single bond.

In the aforesaid Formulas (2), (3a) and (3b), as an aromatic hydrocarbon ring represented by "A", the same aromatic hydrocarbon rings as listed for the above-described $Z_1$ and $Z_2$ are listed for "A". Among these, most preferable is a benzene ring.

In the aforesaid Formulas (2), (3a) and (3b), as an aromatic heterocycle represented by "A", the same aromatic heterocycles as listed for the above-described $Z_1$ and $Z_2$ are listed for "A". Among these, most preferable are a dibenzofuran ring, a dibenzothiophene ring and a carbazole ring.

"n" is preferably an integer of 1 or 2.

The above-described rings and groups may be further substituted with a substituent. Examples of a substituent include groups such as: an alkyl, cycloalkyl, alkenyl, aryl, acylamino, sulfonamide, alkylthio, arylthio, halogen atom, heterocycle, sulfonyl, sulfinyl, phosphonyl, acyl, carbamoyl, sulfamoyl, cyano, alkoxy, aryloxy, heterocyclic oxy, siloxy, acyloxy, carbamoyloxy, amino, alkylamino, imide, ureido, sulfamoylamino, alkoxycarbonylamino, alkoxycarbonylamino, aryloxycarbonylamino, alkoxycarbonyl, aryloxycarbonyl, carboxyl and 2-(2-pyridyl)phenyl group.

When the above-described $Z_1$ and $Z_2$ are substituted with a substituent, a preferred substituent is a 2-(2-pyridyl)phenyl group.

In the aforesaid Formulas (4a), (4b), (5a) and (5b), "A", $Z_1$, $Z_2$ and "n" each respectively indicate the same meaning as represented by "A", $Z_1$, $Z_2$ and "n" in the aforesaid Formulas (1a), (1b), (3a) and (3b). "A" represents an aromatic hydrocarbon ring or an aromatic heterocycle; $Z_1$ represents a non-metallic atomic group necessary to from an aromatic heterocycle; $Z_2$ represents a non-metallic atomic group necessary to from an aromatic hydrocarbon ring or an aromatic heterocycle; and "n" represents an integer of 1 to 4.

Although the aforesaid cupper ion is not specifically limited, there can be cited: CuCl, $CuCl_2$, CuBr, $CuBr_2$, CuI, Cub, CuO, $Cu_2O$, $CuSO_4$, $Cu2SO4$, $CuOCOCH_3$ and $Cu(OCOCH_3)_2$. Among these, preferable are CuI and $Cu_2O$.

Examples of the aforesaid ligand include: aryl alcohols (for example, 2-phenylphenol, 1-naphthol, 2,6-dimethylphenol, salicylaldoxime, N,N-diethylsalicylamide and 8-hydroxyquinoline); alkylamines (for example, 2-(dimethylamino) ethanol and 2-(dimethylamino)glycin); acyclic amines (for example, L-proline and DBU); diamines (for example, 1,2-cyclohexanediamine, N,N'-dimethylethylenediamine and N,N,N',N'-tetramethylethylenediamine); diols (glycols) (for example, ethylene glycol and ethylene glycol dimethyl ether); imidazolium carbenes (for example, 1,3-bis(2,6-diisopropylphenyl)-4,5-dihydroimidazolium tetrafluorobotrate and 1,3-bis(2,6-dimethylphenyl)-4,5-dihydroimidazolium tetrafluorobotrate); pyridines (or called as pyridine compounds) (for example, picolinic acid, 3-methylpicolinic acid, 3-hydroxypicolineamide, 5-methylpicolinic acid, 5-butylpicolinic acid, 6-methylpicolinic acid, 2-aminomethylpyridine and 4-(dimethylamino) pyridine); β-diketones (or called as β-diketone compounds) (for example, acetylacetone, dipivaloylmethane and dibenzoylmethane); and phenanthrolines (for example, 1,10-phenanthroline, 4,7-diphenyl-1,10-phenanthroline, 4,7-dimethyl-1,10-phenanthroline and 3,4,7,8-tetramethyl-1,10-phenanthroline).

Among these, preferable are: picolinic acid, 3-methylpicolinic acid, 6-methylpicolinic acid, 5-butylpicolinic acid, and dipivaloylmethane. More preferable are: picolinic acid, 5-butylpicolinic acid, and dipivaloylmethane.

The typical examples of a compound represented by Formulas (1a) or (1b) of the present invention (more preferably, represented by Formulas (4a) or (4b) of the present invention) are shown below, however, the present invention is not limited to these.

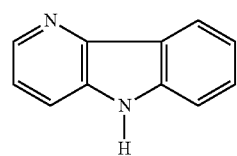

1-1

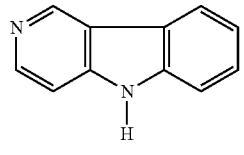

1-2

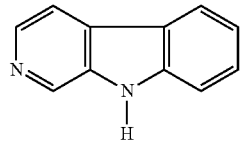

1-3

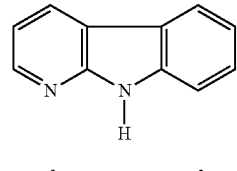

1-4

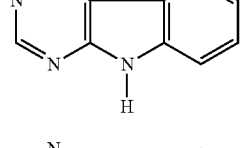

1-5

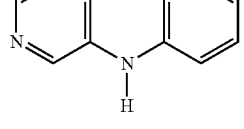

1-6

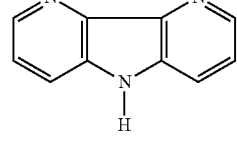

1-7

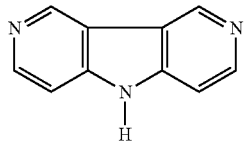

1-8

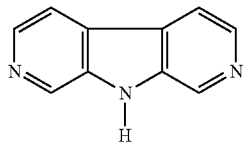

1-9

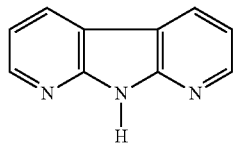

1-10

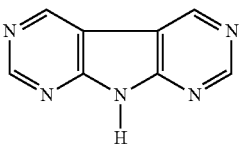

1-11

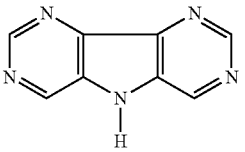

1-12

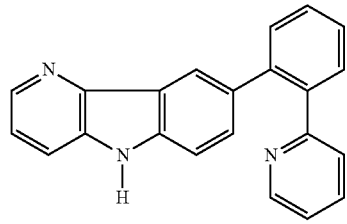

1-13

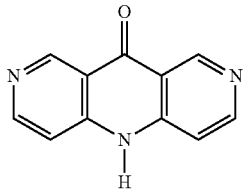

1-14

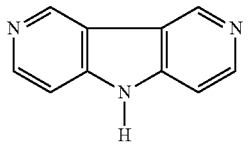

1-15

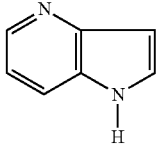

1-16

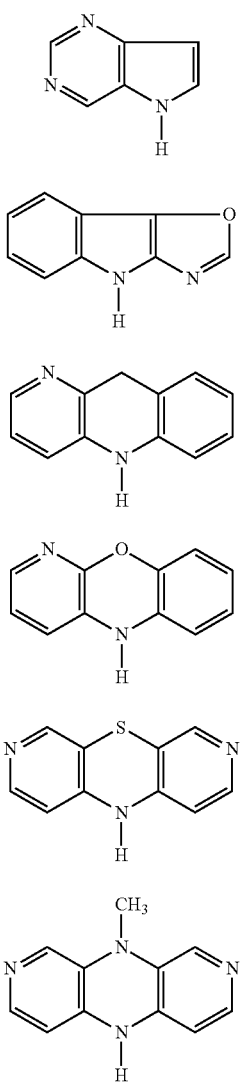
The typical examples of a compound represented by Formula (2) of the present invention are shown below, however, the present invention is not limited to these.
2-4
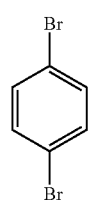
2-5
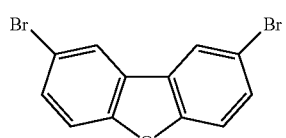
2-6
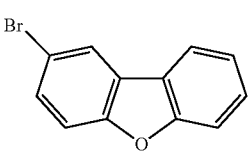
2-7
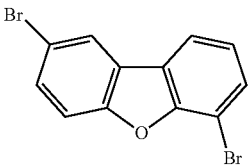
2-8
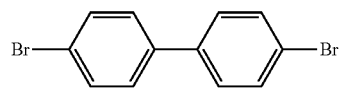
2-9
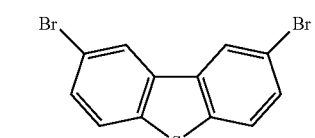
2-10
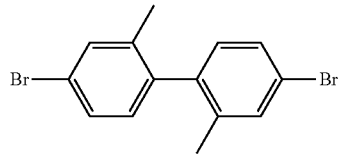
2-11
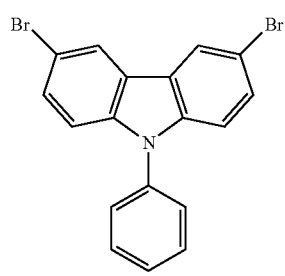

2-12
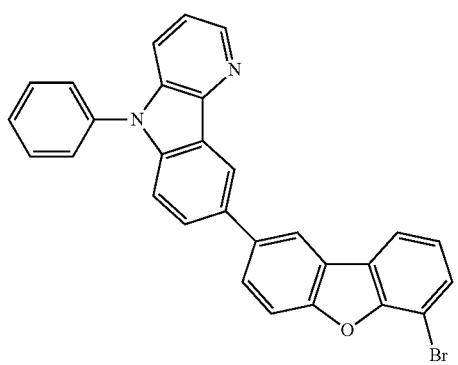
2-13
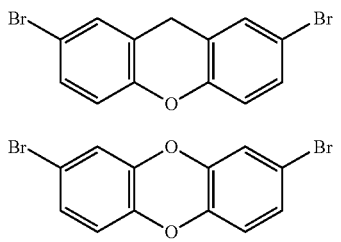
2-14
The typical examples of a nitrogen-containing condensed heterocyclic compound represented by Formulas (3a) or (3b) of the present invention (more preferably, represented by Formulas (5a) or (5b) of the present invention) are shown below, however, the present invention is not limited to these.
3-1
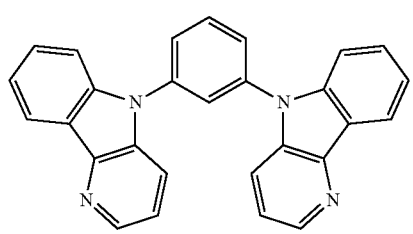
3-2
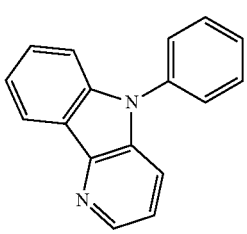
3-3
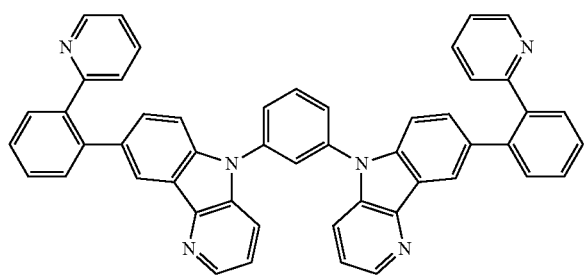
3-4
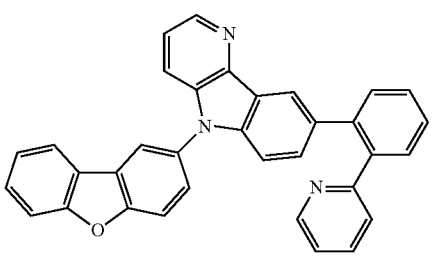
3-5
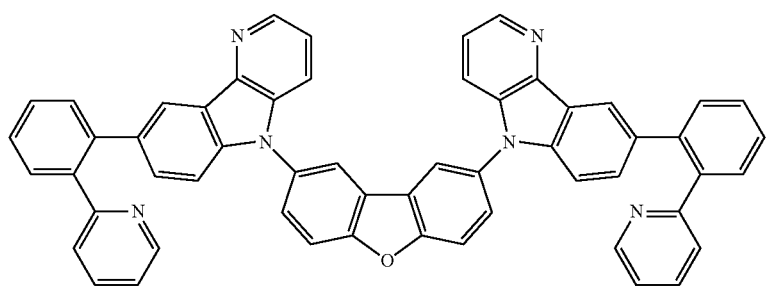
3-6
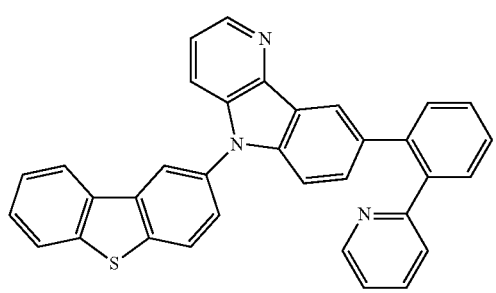

-continued
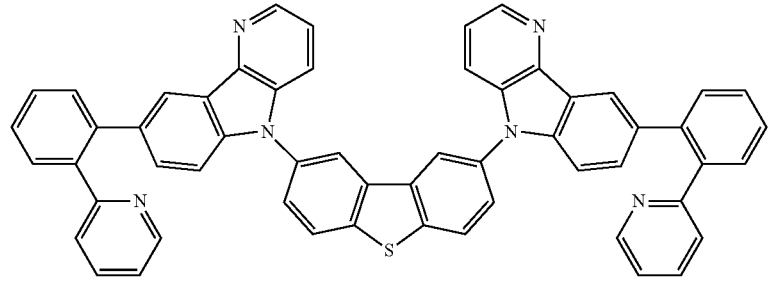
3-7
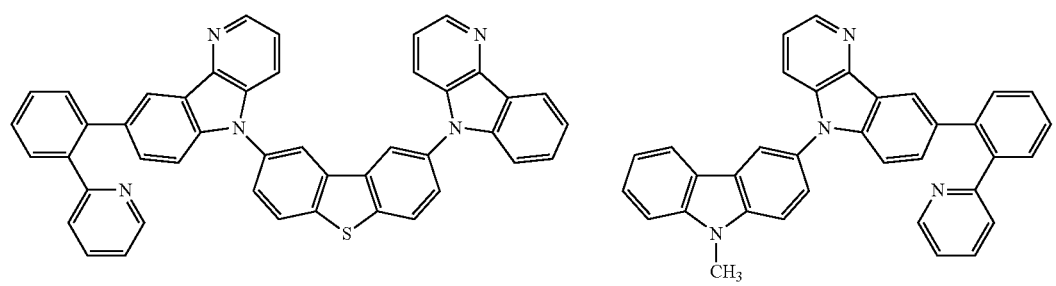
3-8
3-9
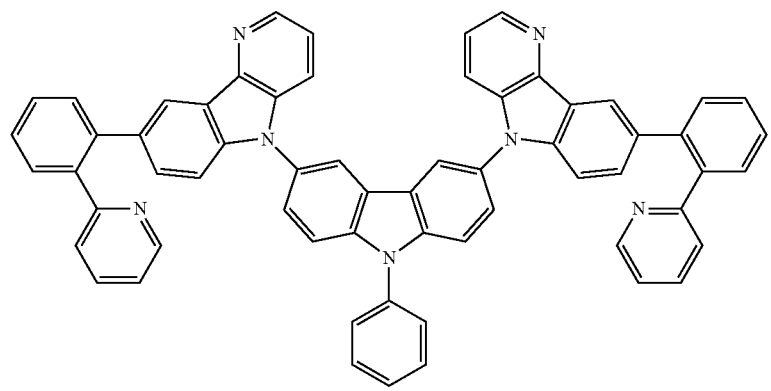
3-10
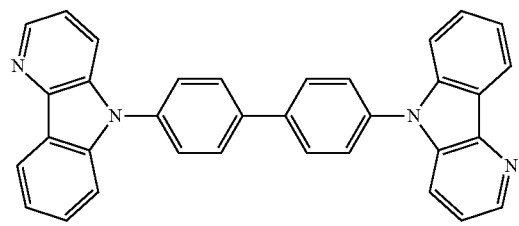
3-11
3-12
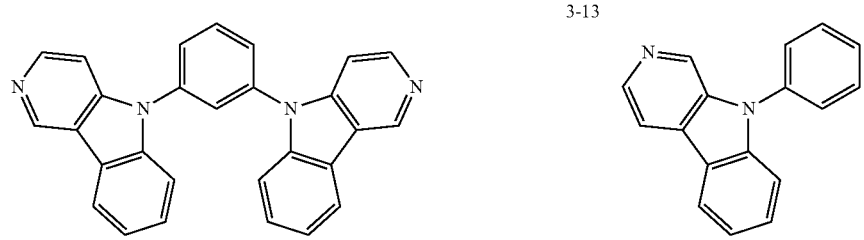
3-13
3-14

-continued
3-15
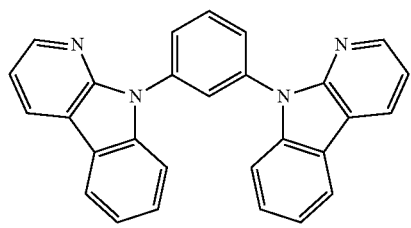
3-16
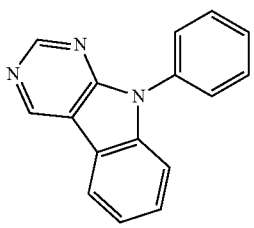
3-17
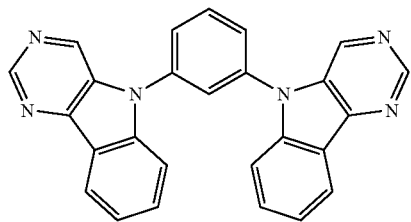
3-18
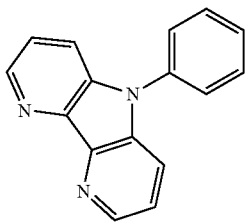
3-19
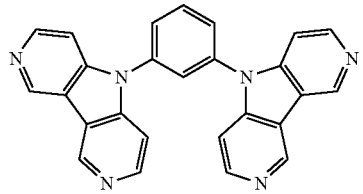
3-20
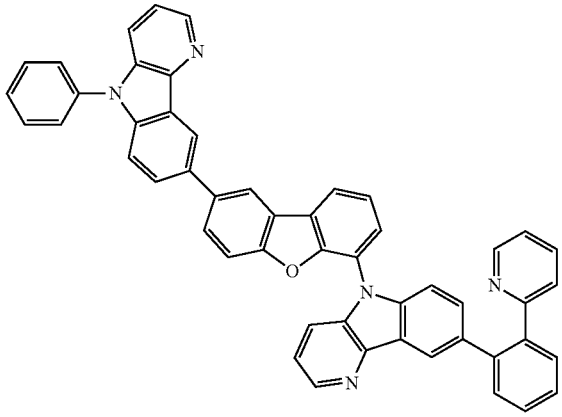
3-21
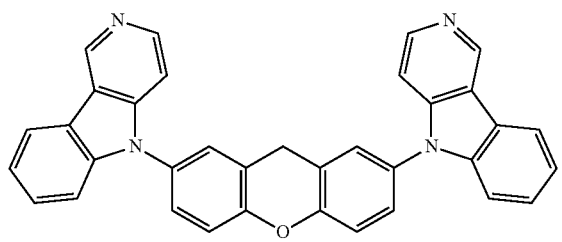
3-22
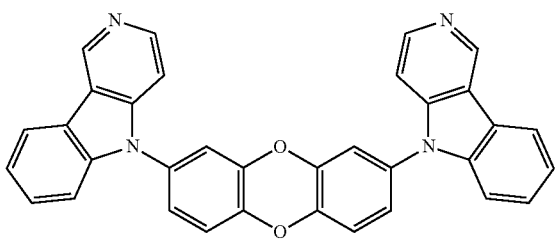
3-23
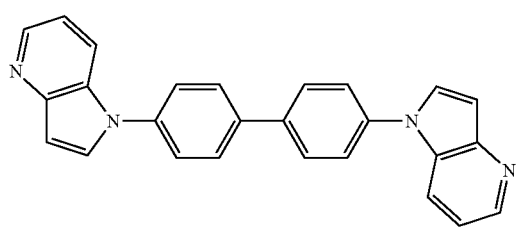
3-24
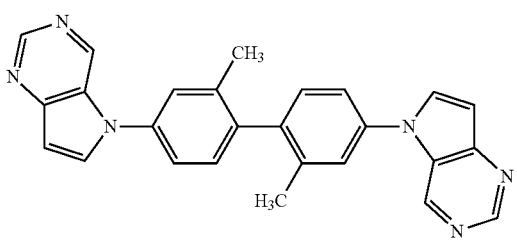

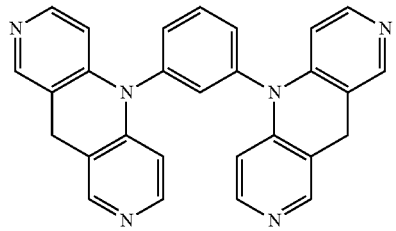

3-25

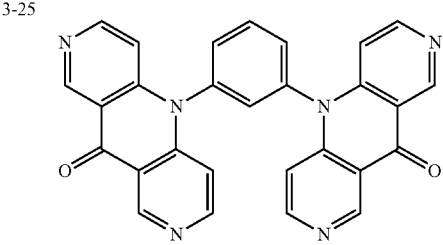

3-26

It is preferable to use a base in the reaction of the present invention. Examples of a base include: alkali metal salts (for example, sodium carbonate, potassium carbonate, sodium hydrogencarbonate, cesium carbonate, cesium fluoride, potassium phosphate, sodium hydroxide, potassium hydroxide and sodium t-butoxide; amine derivatives (for example, triethylamine and tetramethylguanidine). Among these, preferable are potassium carbonate and potassium phosphate, and more preferable is potassium phosphate.

It is preferable to use the aforesaid cupper or cupper ion in an amount of 0.01 to 1 mol with respect to 1 mol of a compound represented by Formula (2). Especially, it is preferable to use the aforesaid cupper or cupper ion in an amount of 0.1 to 0.5 mol.

It is preferable to use the aforesaid ligand in an amount of 0.02 to 1 mol with respect to 1 mol of a compound represented by Formula (2). Especially, it is preferable to use the aforesaid ligand in an amount of 0.2 to 0.8 mol.

Examples of a solvent which can be used are: aprotic solvents (for example, dimethylformamide (DMF), dimethylacetamide (DMAc), dimethylsulfoxide (DMSO) and N-methylpyrrolidone (NMP)); aromatic hydrocarbon solvents (for example, xylene and dichlorobenzene); and ether solvents (for example, ethylene glycol dimethyl ether). Among these, DMSO is more preferable.

The reaction of the present invention is preferably carried out usually in the range of 80 to 200° C., and it is especially preferable to be carried out in the range of 140 to 180° C.

EXAMPLES

Hereinafter, the present invention will be described in details by referring to examples, however, the present invention will not be limited to these. In addition, the "part" or "%" in examples represents "weight part" or "weight %", respectively, if it is not specifically notified.

Example 1

Comparative Synthetic Example 1

The following reaction was carried out as a comparative synthetic example 1 using Cu powders (catalyst) but without using a ligand of the present invention.

<Synthesis of Example Compound 3-20>
(Synthetic Route)

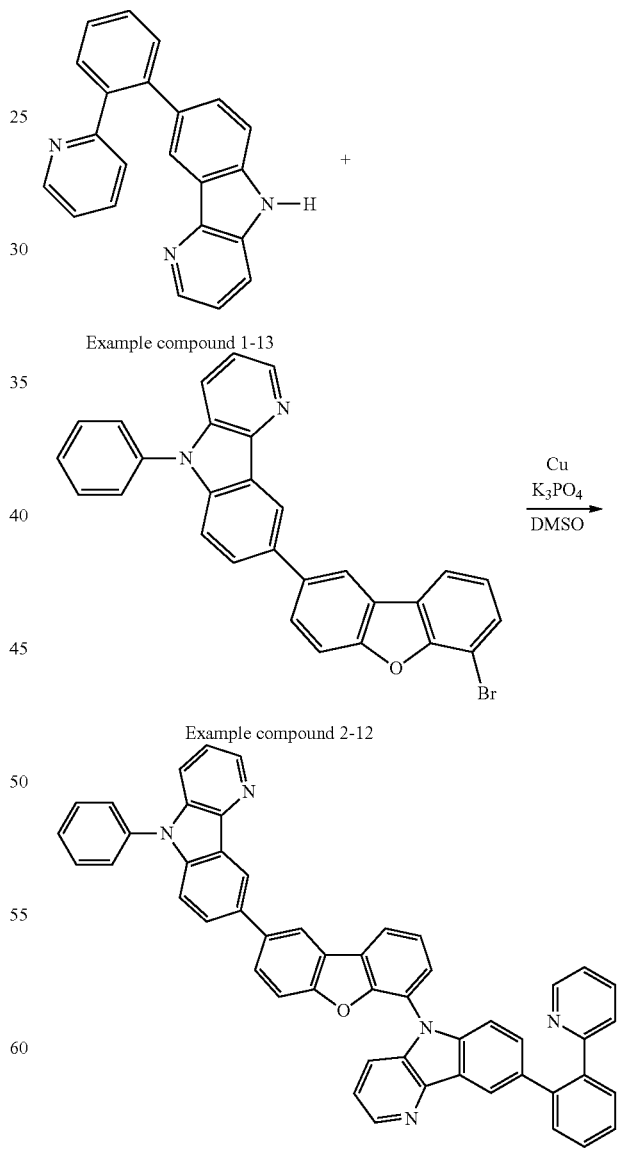

To a reaction vessel were placed 3.3 g (0.0102 mol) of Example compound 1-13, 5.0 g (0.0102 mol) of Example compound 2-12, 3.9 g (0.0102×1.8 mol) of potassium phosphate, 50 ml of DMSO and 1.3 g (0.0102×2.0 mol) of Cu powders under a nitrogen gas flow. The mixture was stirred at 150 to 160° C. for 8 hours. Then, a saturated aqueous sodium chloride solution and THF were added, and after removing insoluble materials, the organic layer was condensed under a reduced pressure. Subsequently, the residue was purified with column chromatography (stationary phase: silica gel; eluent: mixture of toluene/THF). The obtained light brown paste was recrystallized from acetonitrile to produce 0.90 g of Example compound 3-20 (yield=12%).

Synthetic Example 1 of the Present Invention

The following reaction was carried out as a synthetic example 1 of the present invention, using $Cu_2O$ (catalyst) and dipivaloylmethane as a ligand of the present invention.
<Synthesis of Example Compound 3-20
(Synthetic Route)

phate, 50 ml of DMSO, 0.29 g (0.0102×0.20 mol) of $Cu_2O$ and 0.76 g (0.0102×0.40 mol) of dipivaloylmethane as a ligand of the present invention under a nitrogen gas flow. The mixture was stirred at 150 to 160° C. for 8 hours. Then, a saturated aqueous sodium chloride solution and THF were added, and after removing insoluble materials, the organic layer was condensed under a reduced pressure. Subsequently, the residue was purified with column chromatography (stationary phase: silica gel; eluent: mixture of toluene/THF). The obtained light brown paste was recrystallized from acetonitrile to produce 5.2 g of Example compound 3-20 (yield=70%)<

Synthetic Example 2 of the Present Invention

The following reaction was carried out as a synthetic example 2 of the present invention, using $Cu_2O$ (catalyst) and 5-butylpicolinic acid as a ligand of the present invention.
<Synthesis of Example Compound 3-20>
(Synthetic Route)

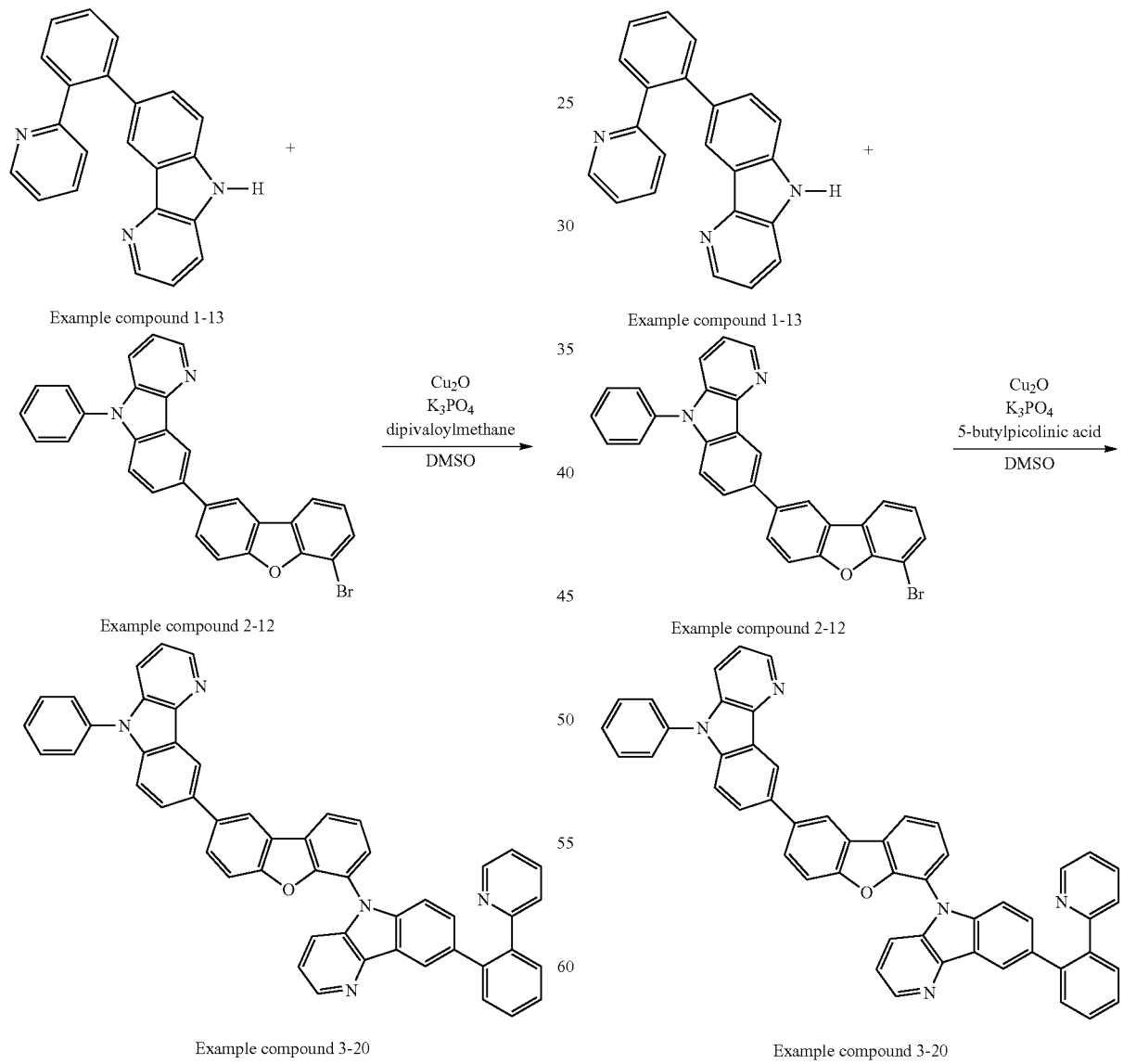

Example compound 1-13

Example compound 2-12

Example compound 3-20

To a reaction vessel were placed 3.3 g (0.0102 mol) of Example compound 1-13, 5.0 g (0.0102 mol) of Example compound 2-12, 3.9 g (0.0102×1.8 mol) of potassium phos- To a reaction vessel were placed 3.3 g (0.0102 mol) of Example compound 1-13, 5.0 g (0.0102 mol) of Example compound 2-12, 3.9 g (0.0102×1.8 mol) of potassium phosphate, 50 ml of DMSO, 0.29 g (0.0102×020 mol) of $Cu_2O$ and 0.73 g (0.0102×0.40 mol) of 5-butylpicolinic acid as a ligand of the present invention under a nitrogen gas flow. The mixture was stirred at 150 to 160° C. for 8 hours. Then, a saturated aqueous sodium chloride solution and THF were added, and after removing insoluble materials, the organic layer was condensed under a reduced pressure. Subsequently, the residue was purified with column chromatography (stationary phase: silica gel; eluent: mixture of toluene/THF). The obtained light brown paste was recrystallized from acetonitrile to produce 5.3 g of Example compound 3-20 (yield=71%)

The $^1H$ NMR data of the produced compound (Example compound 3-20) are shown below.

$^1H$ NMR data (400 MHz, $CDCl_3$): δ=8.79 (d, 1H), 8.67-8.63 (m, 3H), 8.54 (d, 1H), 8.41 (d, 1H), 8.14 (t, 1H), 7.85 (td, 2H), 7.75 (t, 2H), 7.68-7.49 (m, 13H), 7.36 (tt, 3H), 7.15 (dd, 2H), 7.07 (t, 1H) and 6.98 (d, 1H).

The identification of each compound in Examples was performed with a MASS and an NMR spectrum, and each compound was checked to be the object compound, respectively.

Synthetic Example 3 of the Present Invention

The following reaction was carried out as a synthetic example 3 of the present invention, using $Cu_2O$ (catalyst) and picolinic acid as a ligand of the present invention.
<Synthesis of Example Compound 3-19>
(Synthetic Route)

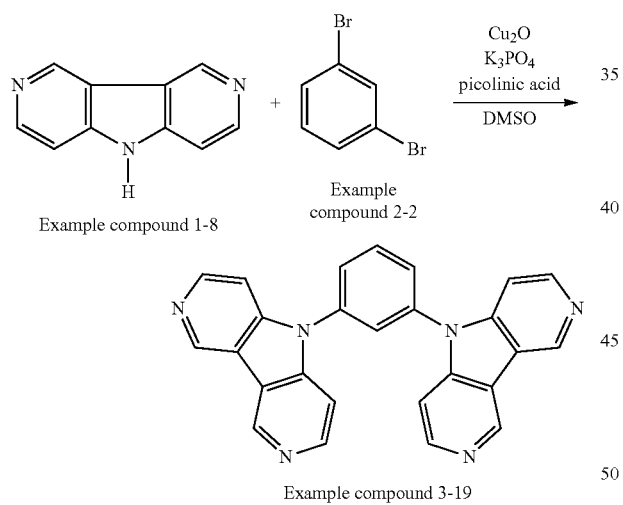

To a reaction vessel were placed 3.44 g (0.0102×2.0 mol) of Example compound 1-18, 2.41 g (0.0102 mol) of Example compound 2-2, 3.9 g (0.0102×1.8 mol) of potassium phosphate, 50 ml of DMSO, 0.29 g (0.0102×0.20 mol) of $Cu_2O$ and 0.50 g (0.0102×0.40 mol) of picolinic acid as a ligand of the present invention under a nitrogen gas flow. The mixture was stirred at 150 to 160° C. for 8 hours. Then, a saturated aqueous sodium chloride solution and THF were added, and after removing insoluble materials, the organic layer was condensed under a reduced pressure. Subsequently, the residue was purified with column chromatography (stationary phase: silica gel; eluent: mixture of toluene/THF). The obtained light brown paste was recrystallized from acetonitrile to produce 2.73 g of Example compound 3-19 (yield=65%). The chemical structure of Example compound 3-19 was confirmed with a MASS and an NMR spectrum. Other example compounds of the present invention illustrated above can also be synthesized in the similar manner as the above-mentioned way.

As clearly shown by the results of the above-described comparative synthetic example 1 and synthetic examples 1 to 3 of the present invention, it was found out that the present invention can provide a production method of a nitrogen-containing condensed heterocyclic compound with a low catalyst amount and a high yield.

It was shown that it can be produced a nitrogen-containing condensed heterocyclic compound useful as an intermediate of an organic synthetic compound or an organic electroluminescence material by using the method of the present invention with a low catalyst amount and a high yield, and the method of the present invention exhibits an excellent effects.

What is claimed is:

1. A method for producing a nitrogen-containing condensed heterocyclic compound comprising the step of:

reacting a compound represented by Formula (4a) with a compound represented by Formula (2) in the presence of $Cu_2O$ or CuO, and a ligand selected from the group consisting of picolinic acid, a 5-butylpicolinic acid and dipivaloylmethane to produce a nitrogen-containing condensed heterocyclic compound represented by Formula (5a):

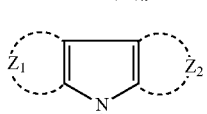

Formula (2)

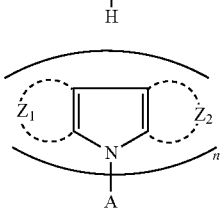

Formula (4a)

Formula (5a)

wherein "A" represents an aromatic hydrocarbon ring or an aromatic heterocycle; $Z_1$ represents a non-metallic atomic group necessary to from an aromatic heterocycle; $Z_2$ represents a non-metallic atomic group necessary to form an aromatic hydrocarbon ring or an aromatic heterocycle; and "n" represents an integer of 1 to 4.

2. The method for producing a nitrogen-containing condensed heterocyclic compound of claim 1,
wherein the reaction is carried out in the presence of a base.

3. The method for producing a nitrogen-containing condensed heterocyclic compound of claim 1,
wherein "A" represents one selected from the group consisting of a benzene ring, a dibenzofuran ring, a dibenzothiophen ring, and a carbazole ring.

4. The method for producing a nitrogen-containing condensed heterocyclic compound of claim 1,
wherein "A" represents one selected from the group consisting of a dibenzofuran ring, a dibenzothiophene ring, and a carbazole ring.

5. The method for producing a nitrogen-containing condensed heterocyclic compound of claim 1,
wherein the ligand is at least one of 5-butylpicolinic acid and dipivaloylmethane.

* * * * *